United States Patent [19]

Heller

[11] 4,182,629

[45] Jan. 8, 1980

[54] PHOTOCHROMIC COMPOUNDS

[76] Inventor: Harold G. Heller, 11 Erwgoch, Waunfawr, Aberystwyth, Dyfed 3AZ, Wales

[21] Appl. No.: 971,037

[22] Filed: Dec. 19, 1978

Related U.S. Application Data

[60] Division of Ser. No. 801,915, May 31, 1977, which is a continuation-in-part of Ser. No. 502,095, Aug. 30, 1974, abandoned.

[30] Foreign Application Priority Data

Sep. 1, 1973 [GB] United Kingdom ............... 41233/73

[51] Int. Cl.$^2$ .......................... G03C 5/24; G03C 1/52
[52] U.S. Cl. ...................................... 430/338; 430/962
[58] Field of Search ................... 96/48 QP, 90 PC; 542/441, 442, 447; 260/326.5 R, 346.74, 346.3, 340.9 R

[56] References Cited

PUBLICATIONS

Hart et al.: Chemical Communication, 1968, pp. 1627–1628.
Santiago et al.: J. Am. Chem. Soc. 90 (1968), pp. 3654–3658.
El-Assal et al.: J. Chem. Soc. (1963), pp. 2983–2988.
Brunow et al.: Acta Chem. Scand. 22 (1965), pp. 590–595.

*Primary Examiner*—Won H. Louie, Jr.
*Attorney, Agent, or Firm*—Fleit & Jacobson

[57] ABSTRACT

Photochromic compounds and useful applications thereof having the general formula:

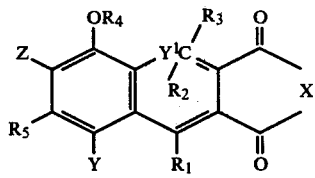

in which X represents oxygen or NR$_6$, R$_6$ being hydrogen, alkyl, aryl or aralkyl, R$_1$ represents hydrogen, alkyl, aryl, or aralkyl, Y and Y$_1$ being the same or different represent hydrogen, alkyl, halogen, or alkoxy, Z represents hydrogen, halogen, alkyl, alkoxy, or aryloxy R$_5$ represents hydrogen, alkyl, alkoxy, or aryloxy, R$_4$ represents alkyl or aryl, and R$_2$ and R$_3$ represent the same or different alkyl, aralkyl or aryl groups or one of R$_2$ and R$_3$ represents hydrogen and the other is alkyl, aralkyl, or aryl, and with the proviso that when Z or Y is alkoxy or aryloxy, R$_1$ is other than hydrogen.

6 Claims, No Drawings

PHOTOCHROMIC COMPOUNDS

This is a divisional of application Ser. No. 801,915, filed May 31, 1977, which, in turn, is a continuation-in-part of application Ser. No. 502,095, filed Aug. 30, 1974, which is abandoned.

FIELD OF THE INVENTION

This invention relates to compounds exhibiting photochromism and useful applications of compounds having this property.

DESCRIPTION OF THE PRIOR ART

Photochromism can be defined as the ability of a material to reversibly change its visible absorption spectrum on exposure to activating radiation and to revert to its original absorption spectrum on removal of the activating radiation or on substituting radiation of a different wavelength.

Organic photochromic compounds have been known for over a hundred years but they excited little commercial interest until the 1950's. In 1955 Y. Hirschberg (J.A.C.S. volume 78, page 2304–2312) investigated three photochromic spiropyrans and one bianthrone derivative which produced coloured forms on exposure to U.V. light and returned to their colourless state on exposure to visible light. Hirschberg measured the rate of formation of the coloured species and vice-versa in various media and concluded that none of the tested compounds would be suitable for the purpose he had in mind, namely date storage, because the rate of colour formation and the rate of bleaching was insufficiently rapid. A further problem encountered by Hirschberg and many subsequent investigators is that the coloured forms tend to be unstable at temperatures approaching normal ambient so that for many compounds the photochromic phenomenon can only be satisfactorily observed at temperatures in the region of $-60°$ C. or below. This obviously makes them unsuitable for practical use in commercial applications. In the search for commercially suitable photochromic compounds, one class of compounds which have been investigated by various workers are derivatives of bismethylene succinic anhydride, which are commonly referred to in the art as "fulgides". These were first described by Stobbe (Chem.Ber. 1904, 37 2236) who discovered a general procedure for their preparation which is still a commonly used process.

Santiago and Becker (J.A.C.S. 1968 90 page 2654) suggested that the primary process by which fulgides form coloured species is a photocyclisation but recognised that competing reactions occurred in the compounds tested. Specific fulgides and related compounds have also been prepared by El-Assal and Shehab (J.Chem. Soc. 1963 pages 3478–82), Brunow et al (Acta.Chem. Scand. 22, 1968, pages 590–5) and by Heller in British Patent No. 1,271,655, but the fulgides described by these workers all show comparatively poor photochromic properties and exhibit irreversible side reactions commonly known as fatique and poor thermal stability. Fatigue products affect the photochromic properties and the properties deteriorate progressively with every colour/erase cycle.

SUMMARY OF THE INVENTION

The present invention is based on a clearer understanding of the mechanism involved in the reversible formation of the coloured products and development of compounds which have a reduced tendency to undergo irreversible side reactions and which also exhibit improved thermal stability.

As a result of this work I have now discovered a series of substituted phenyl methylene succinic anhydrides and succinic imides having markedly improved photochromic properties. The photochromic compounds encompassed by the present invention have the general formula:

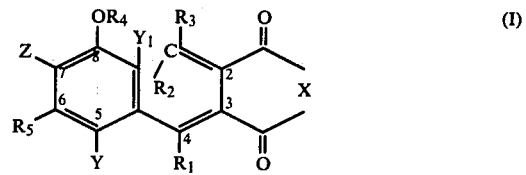

wherein X represents oxygen or $NR_6$, $R_6$ being hydrogen alkyl, aryl or aralkyl.

$R_1$ represents hydrogen, alkyl, aryl or aralkyl,

Y and $Y^1$ are the same or different and represent hydrogen, alkyl, halogen or alkoxy, Z represents hydrogen, halogen, alkyl, alkoxy or aryloxy, $R_5$ represents hydrogen, alkyl, alkoxy or aryloxy, $R_4$ represents alkyl or aryl, and $R_2$ and $R_3$ represent the same or different alkyl, aralkyl or aryl groups or one of $R_2$ and $R_3$ represents hydrogen and the other is alkyl, aralkyl or aryl, with the proviso that when Z or Y is alkoxy or aryloxy, $R_1$ is other than hydrogen.

The aryl groups in the above general formula particularly those at $R_1$, $R_2$, $R_3$ or $R_6$, may be substituted e.g. by halogen, alkyl having 1 to 20 carbon atoms, cycloalkyl having 3 to 12 carbon atoms, aralkyl having 7 to 12 carbon atoms, alkoxy having 1 to 20 carbon atoms or alkaryl groups having 7 to 22 carbon atoms or any combination thereof.

Typical unsubstituted aryl groups are phenyl or naphthyl. Examples of substituted aryl groups are dimethoxyphenyl, piperonyl, methylphenyl, ethylphenyl, isopropylphenyl, t-butylphenyl, sec-butylphenyl, amylphenyl, n-dodecylphenyl and 2,4-dimethylphenyl. Examples of aralkyl groups are benzyl, α-methyl benzyl and α, α-dimethyl-benzyl and examples of suitable cycloalkyl groups are cyclopentyl and cyclohexyl.

DETAILED DESCRIPTION OF THE INVENTION

In the general formula (1) above, where X is oxygen, the compounds are derivatives of succinic anhydride and are conveniently referred to as "fulgides". The corresponding succinic imides (where $X=>NR_6$) are similarly referred to in this specification as "fulgimides".

Compounds of the general formula (1) will on exposure to activating radiation, such as U.V. light, undergo photocylisation to the corresponding naphthalene derivative having the following structural formula (2) below:

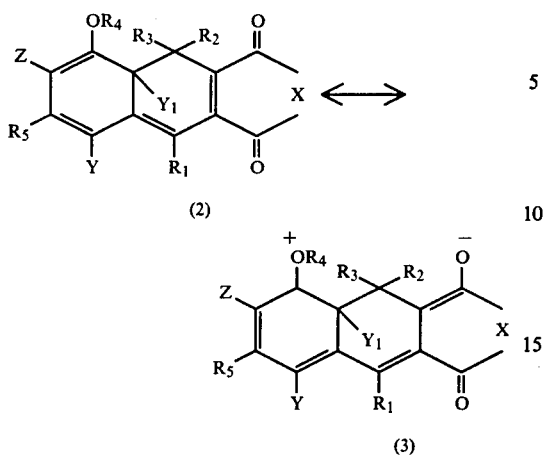

(2)

(3)

The naphthalene derivatives of general formula (2) are resonance stabilised, having a canonical form shown in structural formula (3). It is the series of conjugated double bonds, in the structure shown in formula (3), extending from the $=O^+R^4$ group to the $-O^-$ moiety which is thought to be responsible for the coloured properties of the compounds.

Referring to the numbering in the structural formula (1) the presence of the alkoxy or aryloxy group in the 8 position activates the ring towards electrophilic attack in the positions ortho and para to it, thus facilitating ring closure at these positions. A second alkoxy or aryloxy substituent at the 6 position (i.e. $R_5$) reinforces the activation at the position ortho or $OR_4$ and para to $R_5$. Consequently compounds having alkoxy or aryloxy substituents in both the 6 and 8 positions show a more facile photochemical conversion into the coloured form.

Whereas compounds in which alkoxy or aryloxy substituents are present in both the 6 and 8 positions exhibit pronounced photochromism on exposure to activating radiation, such properties are in general only exhibited in compounds having a 7 or 5 alkoxy or aryloxy substituent when $R_1$ is the structural formula (1) in an alkyl or aryl group.

The reason for this is thought to be that when $R_1$ is hydrogen, cis-trans isomerism is the favoured reaction rather than cyclisation; for example the main reaction on exposing compound (4) below to U.V. light is formation of an isomer via the excited state of having structure (5) below

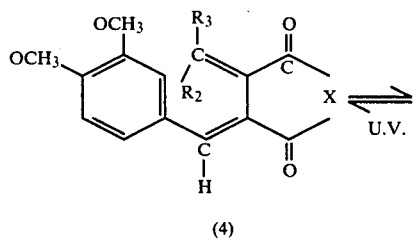

(4)

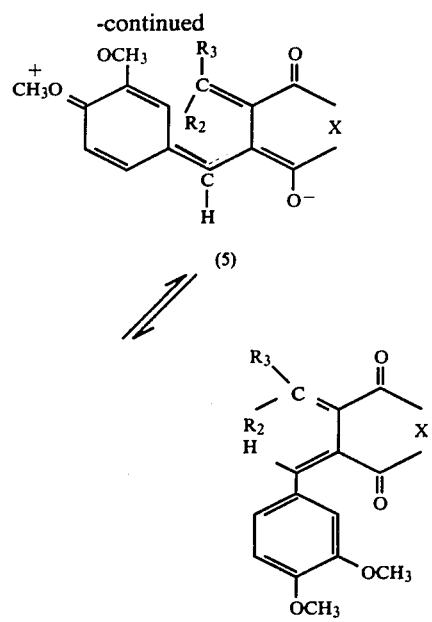

(5)

Compounds of formula (4) are generally non-photochromic or only weakly photochromic. Surprisingly it is found that when $R_1$ is alkyl or aryl (especially a bulky group such as methyl) the cyclisation reaction to compounds of the general formula (2) is again favoured, probably because steric hindrance between the $R_1$ group and the carbonyl groups inhibits coplanarity in the structure.

In compounds of the invention where no alkoxy or aryloxy group is present in the 6 position, it is preferred that the Y position is other than hydrogen since this position is thereby blocked and ring closure in this position is prevented. Otherwise the yield of photochromically active compounds is reduced.

The term "photochromism" is used in the specification to denote a colour change. Such change may be from one coloured form to a differently coloured form or from a colourless form to a coloured form. The term also includes changes which are in intensity or depth of colour rather than from one distinct colour to another.

Provided that the moieties represented by $-OR_4$, $R_5$ and $R_1$ have the identities discussed above, the nature of the remaining substituents can be varied widely within the types of radicals indicated and photochromic compounds obtained which have improved thermal stability and are much less subject to fatique when compared with compounds described in the prior art.

The improved phtochromic properties of the compounds in accordance with the invention makes them suitable for a wide variety of practical applications as photochromic compositions or devices. The commercial applications of the compounds fall into two broad classes (1) those in which a temporary image is formed and (2) those in which use is made of the reduced transmission or reflection of light by the coloured forms.

In the first group of applications the photochromic compounds can be used with advantage in various reproduction, copying and information display systems. Specific examples are as follows.

PHOTOGRAPHY AND REPRODUCTION SYSTEMS

Films or plates may be prepared by coating a support with a solution, dispersion or emulsion containing a compound or mixture of compounds in accordance with the invention. The resulting films or plates can be used as temporary positives or negatives without any need for development or fixing from which permanent prints can be made using conventional photographic materials. The image can be erased and the same photochromic film or plate re-used repeatedly.

Reproduction and copying using plates or films are of particular value in making temporary copies e.g. from microfiche or to prepare a temporary master which can be examined and corrected before a final permanent copy is made.

Information transfer systems are another field in which the compounds of the invention may be used. Government and other organisations often mark classified information in red. Telecopier devices using helium, neon or other red light emitting lasers cannot detect information written in red and photography or other permanent copying of such information is restricted. A temporary copy can be made on a screen bearing a photochromic compound having a bluish coloured form, the information can then be transmitted from the temporary copy and the image erased immediately after use leaving no trace of the classified information and the screen can be re-used many thousands of times.

PHOTOCHROMIC DISPLAY SYSTEMS

Photochromic screens can also be used as information boards, e.g. at railway stations or airports or in special display systems such as flight simulators. The information can be written on the boards with a scanning laser or other light beam device and subsequently erased or updated.

The formation of the coloured cyclic structure is stimulated most effectively by exposure of the compounds to light in the near ultra-violet range, e.g. at about 330–400 mm. On removal of the activating radiation, the compounds will revert to the non-coloured or less coloured form but at normal ambient temperatures the change is not instantaneous. The rate will depend upon the temperature (the higher the temperature, the greater the rate of reversion) and the nature of the substituents. For example, alkoxy substituents in the 6 and 8 positions will increase the half-life of the coloured form, as will the presence of an alkyl or aryl substituent at $R_1$ and alkyl or aryl groups at both $R_2$ and $R_3$. For most of the applications described above it will be necessary or desirable to remove the image at a faster rate than the natural fading rate and this is readily achieved by exposure to a light in the visible spectrum, preferably green light in the range of about 514–550 mm, which can be obtained using an argon ion laser.

The second group of applications make use of the reduced light transmission properties of the coloured forms of the compounds. Thus photochromic packaging film (e.g. coated cellophane) can be used as an outer wrapper to protect products from the effects of sunlight, while allowing the products to be viewed through the wrapping in artificial light. Perishable foodstuffs and pharmaceuticals are examples of products which may be advantageously protected in this way.

Similarly shop windows or storage cabinets may be treated with the compounds of the invention so as to protect their contents. Paints can be formulated with the photochromic compounds so as to reduce the penetration of sunlight, thereby reducing dazzle, extending the life of the paint film or providing camouflage for the military.

For the above uses, the photochromic compounds are normally dispersed in a light transmissive vehicle to form a solution, emulsion or dispersion and then applied as a coating to a support, after which the coninuous phase is removed. Alternatively the compounds may be incorporated within or impregnated into a support, which may be a plate, film, fabric, paper or sheet. Further alternative presentations are as a solid polycrystallite coating, as a large single crystal or as a fluid solution in a cell.

Photochromic compounds in accordance with the invention wherein alkoxy or aryloxy substituents are present in both the 6 and 8 positions form a preferred sub-class of photochromic compounds. In such compounds the substituents in the 6 and 8 positions act as auxochromic groups giving rise to strong absorbtion in 500 to 600 mm waveband and typical maxima at about 550 mm. This gives the coloured forms a deep purple to dark blue appearance. Additional thermal stability is also observed with compounds of this sub-class, which is thought to arise from resonance between the excited state indicated in formula (3) above and a similar structure in which the positive charge falls on the alkoxy or aryloxy group in the 6-position.

Because of ease of preparation using available starting materials, compounds in which the 6 and 8 substituents are both alkoxy are preferred to the corresponding compounds in which the substituents are aryloxy groups. Preferably the alkoxy groups are lower alkoxy (1 to 5 carbon atoms), methoxy being especially preferred.

The alkyl or aryl groups represented by $R_2$ and $R_3$ may be varied widely but preferably are lower alkyl (1 to 5 carbon atoms).

Examples of specific compounds falling within the scope of the present invention are as follows:

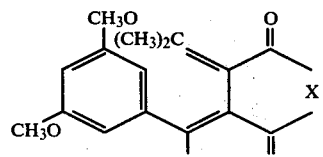

wherein $X = -O-$ or $>N$ Phenyl.

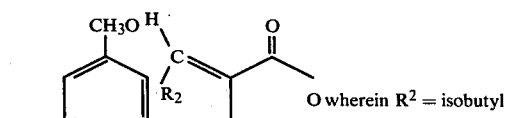

O wherein $R^2 =$ isobutyl

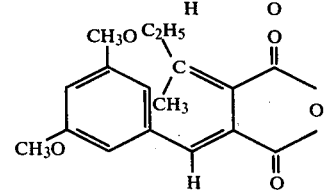

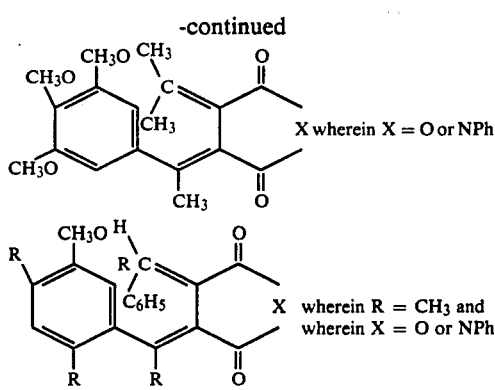

X wherein X = O or NPh

X wherein R = CH₃ and wherein X = O or NPh

The compounds of the present invention can be prepared by condensing an aldehyde or ketone of the formula (6)

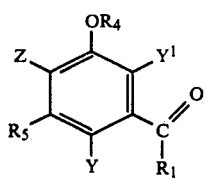

with an ester of a succinic acid derivative of the formula (7)

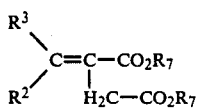

wherein $R_1$, $R^2$, $R^3$, $R^4$, $R^5$, Y, $Y^1$ and Z are as defined above and $R_7$ is the residue of an alcohol, by a Stobbe condensation, hydrolysing the half ester produced to form the di-acid, and then heating the resulting di-acid with an acid chloride to give a product of formula (1) wherein X is oxygen.

The Stobbe condensation is carried out by refluxing the reactants in t-butanol containing potassium t-butoxide if vigorous conditions are required, or with sodium hydride in anhydrous ether if mild reaction conditions are needed. Preferably potassium t-butoxide in t-butanol is used. The product of this stage of the reaction is the half ester, i.e. where one $R^7$ group is hydrogen. This is then converted into the di-acid by hydrolysis, e.g. by boiling with aqueous potassium hydroxide solution. The di-acid is then converted into its anhydride by a dehydration reaction comprising heating with an acid chloride. Preferably acetyl chloride is used.

The compounds of formula (1) produced in this way in which X is oxygen can be converted into those where X is $>NR_6$ by heating equimolar proportions of the anhydride and the primary amine $R_6NH_2$ to produce the corresponding half amide. The half amide is then converted into the desired compound by heating with an acid chloride or acid anhydride such as acetyl chloride or acetic anhydride. The reaction with the amine may be carried out in an organic solvent if desired, e.g. ethanol or benzene.

An alternative method of preparing compounds of formula 1 in which X is $>NR_6$ is to react the half ester product of the Stobbe condensation with a compound of the formula $R_6NHMgBr$ to produce the corresponding succinamic acid, i.e. wherein the group —$COOR_7$ becomes —$CONHR^6$. This is then dehydrated by reaction with an acid chloride such as acetyl chloride.

The Stobbe condensation is a procedure of general application for the synthesis of fulgides in accordance with the invention as well as starting materials of formula (7). A fairly comprehensive account of the Stobbe condensation and its application to the synthesis of succinic acid derivative can be found in Chapter 1 of volume 6 of "Organic Reactions" published by Wiley, New York, 1951, pages 1 to 73.

Fulgimides in which $R_6$ is hydrogen may be prepared by reacting the appropriate succinic anhydride with concentrated ammonia to produce the corresponding half amide acid and then reacting the product with diazomethane to yield the methyl ester of the half amide, followed by cyclisation using sodium ethoxide. This procedure is fully described in the paper by Goldschmidt et al, published in Liebigs Annalen der Chemie, 1957, volume 604, pages 121 to 132.

The invention will be illustrated with reference to the following Examples in which parts are parts by weight unless otherwise indicated.

EXAMPLE 1

Preparation of (E)-3,5-dimethoxybenzylidene isopropylidenesuccinic anhydride.

3,4-dimethoxybenzaldehyde (7.8 parts) and diethyl isopropylidenesuccinate (10 parts) were added to a boiling solution of potassium t-butoxide (5 parts) in t-butanol (70 parts by volume). After 10 minutes, the reaction mixture was cooled, the solvent removed and the residual oil acidified with hydrochloric acid. The liberated (E)-3,5-dimethoxybenzylidene isopropylidenesuccinic half ester was recrystallised from ethanol, m.p. 109°–110° C.

The half-ester (3 parts) was hydrolysed by boiling with 5% aqueous potassium hydroxide solution and the diacid precipitated by the addition of hydrochloric acid. The dried diacid was dissolved in acetyl chloride (100 parts by volume), boiled for 1 hour and the solvent removed. The residual oil was crystallised from benzene/petrol mixture to give (E)-3,5-dimethoxybenzylidene isopropylidenesuccinic anhydride (1.6 parts) in the form of yellow needles, m.p. 161°–162° C., which on irradiation at 366 nm, turn blue. The colour is reversed on exposure to white light.

By condensing the appropriate substituted succinic ester with 3,5-dimethoxybenzaldehyde, according to the above procedure the following compounds were prepared:

(E)-3,5-dimethoxybenzylidene (E)-2-butylidenesuccinic anhydride (E)-3,5-dimethoxybenzylidene (Z)-2-butylidenesuccinic anhydride (E)-3,5,dimethoxybenzylidene (E)-isobutylidenesuccinic anhydride

EXAMPLE 2

(E)-3,5-dimethoxybenzylidene isopropylidene-succinic half ester (3 parts), prepared as in Example 1, in ether was added to an excess of anilinomagnesium bromide in ether, and the reaction mixture boiled for 15 minutes, cooled and acidified with hydrochloric acid. The liberated succinamic acid was filtered off and recrystallised from ethanol. The dry acid was dissolved in acetyl chloride (100 parts by volume) boiled for 1 hour and the solvent removed. Crystallisation of the product from a benzene/petrol mixture gave (E)-3,5-dimethoxybenzylidene isopropylidene-N-phenylsuccinimide as yellow needles, m.p. 168°–169° C. The compound shows similar photochromic properties to the corresponding anhydride.

EXAMPLE 3

Preparation of (E) and (Z)-α-(3,4,5-trimethoxyphenyl) ethylidene-isopropylidenesuccinic anhydrides.

3,4,5-trimethoxyacetophenone (5 parts) and diethyl isopropylidenesuccinate (5 parts) were added to a boiling solution of potassium t-butoxide (2.8 parts) in t-butanol. Work up by the method described in Example 1 gave the half ester which was hydrolysed to the diacid (2.7 parts) with 5% aqueous potassium hydroxide solution followed by acidification with hydrochloric acid. The di-acid was dried and heated for 1 hour with acetyl chloride (20 parts by volume) and the solvent removed. Recrystallisation of the residual oil from benzene/petrol gave (E)-α-(3,4,5-trimethoxypenyl)-ethylidene isopropylidenesuccinic anhydride as pale yellow cubes, m.p. 139°–140° C., which turn deep blue on irradiation at 366 nm. The colour is reversed with white light.

The (Z) isomer was obtained in a later crop of crystals, which on irradiation at 366 nm. photoisomerise to the (E) isomer which shows photochromic properties. (E)-α-(3,5-dimethoxyphenyl) ethylidene isopropylidenesuccinic anhydride was obtained in an analogous reaction starting from 3,5-dimethoxyacetophenone.

EXAMPLE 4

(E)-α-(3,4,5-trimethoxyphenyl) ethylideneisopropylidene succinic anhydride (4 parts), prepared as in Example 3, in toluene (40 parts by volume), and aniline (1 part) were heated (12 hours) at 70°. Petrol was added and the liberated succinamic acid separated. The dry acid (1.8 parts) was dissolved in acetyl chloride (40 parts by volume) boiled for 2 hours and the solvent removed. Crystallisation of the product from a toluene/petrol mixture gave (E)-α-(3,4,5-trimethoxyphenyl) ethylideneisopropylidene-N-phenylsuccinimide as pale yellow needles, melting point 169.5°. The compound shows similar photochromic properties to the corresponding (E)-anhydride.

EXAMPLE 5

Preparation of (E)- and (Z)-α-3,5-dimethoxyphenylethylidene (isopropylidene) succinic anhydrides.

3,5-dimethoxyacetophenone (4.2 parts) and diethyl isopropylidene succinate (4.9 parts) in benzene (20 parts by volume) were added to a stirred suspension of sodium hydride (1 part) in benzene (100 parts by volume). When reaction was complete, a small amount of ethanol was added to destroy excess sodium hydride, the solvent was removed, and the residual oil acidified with hydrochloric acid. The resulting half ester (5 parts) was hydrolysed with 2% ethanolic potassium hydroxide solution and the diacid precipitated by addition of hydrochloric acid. The dried acid (3.5 parts) was boiled with acetyl chloride (50 parts by volume) for 1 hour and the solvent removed. The (E)- and (Z)-anhydrides were separated by fractional crystallisation from toluene and light petroleum giving pale yellow crystals, m.p. 146°–147° and 124°–126°, respectively, which on irradiation at 366 nm turn blue. The colour is reversed on exposure to while light.

(E,E)-Benzylidene-α3,4,5-trimethoxyphenylethylidenesuccinic anhydride can be prepared by a similar procedure using 3,4,5-trimethoxyacetophenone and diethyl (E)-benzylidene succinate as reactants. The anhydride is obtained as yellow cubes, m.p. 181° which show similar photochromic properties.

The following Examples are given to illustrate the production of photochromic films and screens in accordance with the invention.

EXAMPLE 6

10 grams of the pale yellow crystals obtained in Example 3 were dissolved, together with 100 grams of cellulose acetate, in 1 liter of a 50/50 volume mixture of 2-hydroxy ethyl acetate and acetone. The resulting solution was filtered and coated onto a cellulose acetate base sheet using a blade over roller coating technique to achieve a wet coating thickness of 120 microns. After drying at 120° C., the coating had a dry thickness of about 12 microns. The resulting screen produced a deep blue image when exposed to a light beam having a wavelength of 366 nm, the image being extinguished by subsequent exposure to a light beam at 550 nm and could be used as a display screen. Screens of higher optical quality can be produced using glass plates in place of cellulose acetate film.

EXAMPLE 7

A solution containing 10 grams of the crystals obtained in Example 1 were dissolved in 1 liter of toluene with warming. A piece of "Wratten" 50 grade paper was dipped into the solution, removed and dried in air at room temperature. A blue image was obtained by exposing the impregnated paper to light of wavelength 366 nm and, the impregnated paper was suitable for making temporary copies e.g. from microfiche, under normal ambient temperatures.

I claim:

1. A method of forming a temporary image on a surface using activating radiation which comprises the steps of:

(a) forming a photochromic surface comprising a photochromic compound having the general formula (1) below and a support therefor,

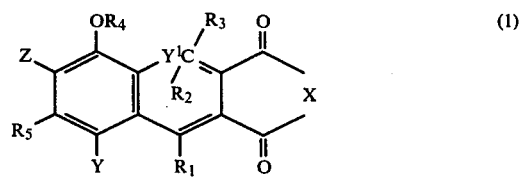

wherein X represents oxygen or >NR$_6$, R$_6$ being hydrogen, alkyl, aryl or aralkyl, R$_1$ represents alkyl, aryl or aralkyl, Y and Y$^1$ are the same or different and represent hydrogen, alkyl, halogen or alkoxy, Z represents hydrogen, halogen, alkyl, alkoxy or aryloxy, R$_5$ represents hydrogen, alkyl, alkoxy or aryloxy, R$_4$ represents alkyl, aryl or aralkyl and $R_2$ and $R_3$ represent the same or different alkyl, aryl, or aralkyl groups or one of $R_2$ and $R_3$ represents hydrogen and the other is alkyl, aryl or aralkyl, and (b) subjecting the photochromic surface to activating radiation using imaging means whereby areas of the surface exposed to the radiation exhibit a colour change or tone resulting from reversible photocyclisation of the photochromic compound.

2. The method of claim 1 wherein the activating radiation is U.V. light having a wavelength in the range of about 330 to 400 nm.

3. The method of claim 2 wherein the photochromic surface comprises light-transmissive matrix having said photochromic compound dispersed therein or coated thereon.

4. A method of forming a temporary image on a surface using activating radiation which comprises the steps of:

(a) forming a photochromic surface comprising a photochromic compound having the general formula:

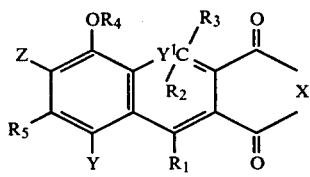

wherein X represents oxygen or $>NR_6$, $R_6$ being hydrogen, alkyl or aryl, $R_1$ represents hydrogen, alkyl or aryl, Y and $Y^1$ are the same or different and represent hydrogen, alkyl or halogen, Z represents hydrogen, halogen or alkyl, $R_5$ represents alkoxy or aryloxy, $R_4$ represents alkyl or aryl and $R_2$ and $R_3$ represent the same or different alkyl, aralkyl or aryl groups or one of $R_2$ and $R_3$ represents hydrogen and the other is alkyl, or aryl and (b) subjecting the photochromic surface to activating radiation using imaging means whereby areas of the surface exposed to the radiation exhibit a colour change or tone resulting from reversible photocyclisation of the photochromic compound.

5. A photochromic image recording or display device which comprises a photochromic compound having the general formula (1) below:

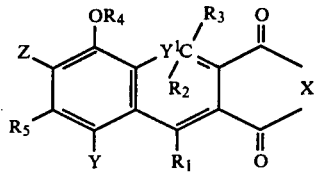

wherein X represents oxygen or $>NR_6$, $R_6$ being hydroge, alkyl, aryl or aralkyl, $R_1$ represents alkyl, aryl or aralkyl, Y and $Y^1$ are the same or different and represent hydrogen, alkyl, halogen or alkoxy, Z represents hydrogen, halogen, alkyl, alkoxy or aryloxy, $R_5$ represents hydrogen, alkyl, alkoxy or aryloxy, $R_4$ represents alkyl, aryl or aralkyl, and $R_2$ and $R_3$ represent the same or different alkyl, aryl, or aralkyl groups or one of $R_2$ and $R_3$ represent hydrogen and the other is alkyl, aryl or aralkyl, said photochromic compound being in the form of a coating on a support or dispersed in a light-transmitting matrix.

6. A photochromic image recording or display device which comprises a photochromic compound having the general formula:

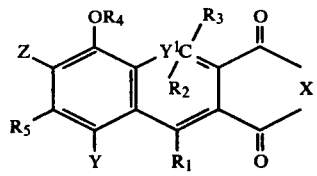

wherein X represents oxygen or $>NR_6$, $R_6$ being hydrogen, alkyl or aryl, $R_1$ represents hydrogen, alkyl or aryl, Y and $Y^1$ are the same or different and represent hydrogen, alkyl or halogen, Z represents hydrogen, halogen or alkyl, $R_5$ represents alkoxy or aryloxy, $R_4$ represents alkyl or aryl, and $R_2$ and $R_3$ represent the same or different alkyl, aryl or aralkyl groups or one of $R_2$ and $R_3$ represent hydrogen and the other is alkyl, or aryl said photochromic compound being in the form of a coating on a support or dispersed in a light-transmitting matrix.

* * * * *